United States Patent
Münnich et al.

(10) Patent No.: US 7,763,757 B2
(45) Date of Patent: Jul. 27, 2010

(54) CRYSTALLIZATION PROCESSES FOR PRODUCING BISPHENOLS

(75) Inventors: Christian Münnich, Leverkusen (DE); Ulrich Blaschke, Krefeld (DE); Rob Eek, HongKong (CN); Michael Prein, Krefeld (DE); Raymond Audenaert, Hamme (BE); Gert Tytgat, Duffel (BE)

(73) Assignee: Bayer Material Science AG, Leverkusen (DE)

( * ) Notice: Subject to any disclaimer, the term of this patent is extended or adjusted under 35 U.S.C. 154(b) by 204 days.

(21) Appl. No.: 11/971,268

(22) Filed: Jan. 9, 2008

(65) Prior Publication Data

US 2008/0200734 A1    Aug. 21, 2008

(30) Foreign Application Priority Data

Jan. 9, 2007   (DE) ................. 10 2007 001 427

(51) Int. Cl.
*C07C 37/84* (2006.01)
*C07C 39/16* (2006.01)

(52) U.S. Cl. .................... 568/724; 568/727
(58) Field of Classification Search ............ 568/717
See application file for complete search history.

(56) References Cited

U.S. PATENT DOCUMENTS

| | | | |
|---|---|---|---|
| 4,391,997 A | | 7/1983 | Mendiratta |
| 4,400,555 A | | 8/1983 | Mendiratta |
| 4,590,303 A | | 5/1986 | Mendiratta |
| 4,638,102 A | * | 1/1987 | Little .................. 568/724 |
| 5,245,088 A | * | 9/1993 | Fimuro et al. ........... 568/724 |
| 5,545,764 A | | 8/1996 | Berg et al. |
| 6,828,465 B2 | | 12/2004 | Neumann et al. |
| 2004/0030195 A1 | | 2/2004 | Neumann et al. |
| 2007/0004941 A1 | * | 1/2007 | Blaschke et al. .......... 568/728 |

FOREIGN PATENT DOCUMENTS

| | | |
|---|---|---|
| EP | 0 210 366 A1 | 2/1987 |
| EP | 0 671 377 | 9/1995 |
| EP | 1 268 379 B1 | 1/2003 |
| EP | 1 607 380 A1 | 12/2005 |
| EP | 1 728 777 | 12/2006 |

* cited by examiner

*Primary Examiner*—Brian J Davis
(74) *Attorney, Agent, or Firm*—Connolly Bove Lodge & Hutz LLP

(57) ABSTRACT

Processes for producing bisphenols (e.g., bisphenol A (BPA)) having a purity greater than 99.7% are described, such processes including reacting a phenol and acetone in the presence of an acidic catalyst to form a product mixture comprising a bisphenol; removing at least a portion of the bisphenol from the product mixture in the form of a bisphenol/phenol adduct by crystallization, filtration and washing to provide bisphenol/phenol adduct crystals; and removing at least a portion of the phenol from the bisphenol/phenol adduct crystals to provide the bisphenol having a purity of more than 99.7%; wherein the crystallization comprises continuous suspension crystallization and is carried out in at least three crystallization devices arranged such that the product mixture is first cooled in a first stage of the crystallization to a temperature of 50 to 70° C. in a first crystallization device and a second crystallization device connected in parallel, and subsequently cooled in a second stage of the crystallization to a temperature of 40 to 50° C. in a third crystallization device connected downstream in series to the first and second crystallization devices, and wherein a total dwell time of the product mixture in the crystallization is more than 4 hours.

18 Claims, 2 Drawing Sheets

CRYSTALLIZATION PROCESSES FOR PRODUCING BISPHENOLS

BACKGROUND OF THE INVENTION

As condensation products of phenols and carbonyl compounds, bisphenols are starting substances or intermediate products for the production of a multiplicity of products. Of particular technical importance is the condensation product which results from the reaction between phenol and acetone, namely 2,2-bis(4-hydroxyphenyl)propane (i.e., bisphenol A, or "BPA"). BPA can be used as a starting substance for the production of diverse polymeric materials, such as, for example, polyarylates, polyetherimides and modified phenolformaldehyde resins. Preferred fields of application for BPA as a starting material include the production of epoxy resins and polycarbonates.

Methods for the synthesis of bisphenol A (BPA) by means of ion exchanger catalysis are disclosed, for example, in U.S. Pat. No. 4,391,997, U.S. Pat. No. 4,400,555, U.S. Pat. No. 4,590,303, and European Patent Application EP 0210366A. It is also known to produce BPA on a large scale by passing a mixture of phenol and acetone through a fixed bed reactor packed with polystyrene-based sulfonic acid ion exchanger resins and then working it up.

The reaction of phenol with acetone in the presence of acidic catalysts produces a product mixture (reaction mixture) that can contain, in addition to unreacted phenol and possibly acetone, primarily BPA and water. In addition, typical by-products (minor constituents) of the condensation reaction occur in small amounts, for example, 2-(4-hydroxyphenyl)-2-(2-hydroxyphenyl)propane (i.e., o,p-BPA), substituted indanes, hydroxyphenylindanols, hydroxyphenylchromanes, substituted xanthenes and more highly condensed compounds containing three or more phenyl rings in the molecular structure. In addition, further minor constituents, such as anisole, mesityl oxide, mesitylene and diacetone alcohol, may form by self-condensation of the acetone and reaction with impurities in the raw materials.

Such by-products, as well as water, phenol and acetone, can adversely affect the suitability of BPA for the production of polymers and generally have to be removed by suitable processes. In particular, high purity requirements are imposed on the BPA raw materials used in the production of many polycarbonates.

Working-up and purification methods for BPA can be performed by removing BPA from the reaction mixture in the form of an approximately equimolar crystalline adduct containing phenol by cooling the reaction mixture and crystallizing out the BPA/phenol adduct in a suspension crystallization. The BPA/phenol adduct crystals can then be removed from the liquid phase by a suitable solid/liquid separation apparatus, such as a rotary filter or centrifuge, and purified further.

Adduct crystals obtained in this way can typically have a purity of more than 99% BPA relative to the minor constituents, with a phenol component of approximately 40%. Superficially adhering impurities can be removed from the adduct crystals by washing with suitable solutions that typically contain one or more constituents from the group comprising acetone, water, phenol, BPA and minor constituents.

The BPA/phenol adduct crystals obtained following the above-described suspension crystallization of the reaction solution and the solid/liquid separation are generally subjected to further purification steps that can include, for example, distillative, desorptive or extractive methods in which the removal of phenol and possibly the reduction of the concentration of minor constituents in BPA can be achieved.

Alternatively, the phenol can also be removed from the BPA/phenol adduct crystals by melting processes.

As mentioned, high requirements are imposed on the extraction of BPA/phenol adduct crystals from the product mixture. Therefore, in addition to the phenol present in excess, and possibly unreacted acetone, the process should also generally remove water and a multiplicity of other by-products of the bisphenol A production, such as, for example, the aforementioned 2-(4-hydroxyphenyl)-2-(2-hydroxyphenyl)propane, substituted indanes, hydroxyphenylindanols, hydroxyphenylchromanes, spirobisindanes, substituted indanols, substituted xanthenes and more highly condensed compounds containing three or more phenyl rings in the molecular structure.

Thus, for example, European Patent No. 1268379 B1 describes a process for producing BPA/phenol adduct crystals by crystallization. The production of BPA having a purity of 99.5% is described, preferably by a two-stage crystallization in which the product mixture is first cooled to around 50 to 70° C. and then to 40 to 50° C.

Since the purity requirements imposed on bisphenol A are always increasing, further process improvements are desired to ensure the increasing quality requirements, for example, for the production of polycarbonate.

This can be made possible, for example, by increasing the dwell time in the crystallizers. Thus, for example, it is known from European Patent Application No. 1607380 A1, that in the case of a short dwell time of 0.5 h or less in crystallization and correspondingly faster crystallization, the inclusion of reaction mixture or, in other words, the incorporation of impurities in the BPA/phenol adduct crystals result in a poorer bisphenol A quality, with the result that dwell times in the region of 1-3 h are preferred.

A further disadvantage of the method described in European Patent No. 1268379 B1 is that, in the case of such a two-stage crystallization, deposits may occur at the surfaces (fouling) in the circulation coolers of the 1st stage of the crystallization (high-temperature stage). To remove the deposits by heating to approximately 80° C., for example, the circulating cooler has to be shut down at regular intervals to remove the deposits by melting. During this time, the production has to be stopped or the crystallization has to be taken over by the second crystallization stage alone. This can result in production loss and/or reduced product quality characterized, for example, by an increased proportion of by-products (impurities) in the BPA.

BRIEF SUMMARY OF THE INVENTION

The present invention relates, in general, to processes for producing bisphenols of high purity. More particularly, the present invention relates to processes for producing bisphenols, preferably bisphenol A (BPA), with purities greater than 99.7%.

One object of the present invention was to provide a process for producing a bisphenol having a purity of >99.7%, accompanied by a simultaneous prolonging of the time interval between shut downs of the high-temperature crystallization stage for the removal of fouling deposits by melting.

One embodiment of the present invention includes a process comprising:

(a) reacting a phenol and acetone in the presence of an acidic catalyst to form a product mixture comprising a bisphenol;

(b) removing at least a portion of the bisphenol from the product mixture in the form of a bisphenol/phenol adduct by crystallization, filtration and washing to provide bisphenol/phenol adduct crystals; and (c) removing at least a portion of the phenol from the bisphenol/phenol adduct crystals to provide the bisphenol having a purity of more than 99.7%;

wherein the crystallization comprises continuous suspension crystallization and is carried out in at least three crystallization devices arranged such that the product mixture is first cooled in a first stage of the crystallization to a temperature of 50 to 70° C. in a first crystallization device and a second crystallization device connected in parallel, and subsequently cooled in a second stage of the crystallization to a temperature of 40 to 50° C. in a third crystallization device connected downstream in series to the first and second crystallization devices, and wherein a total dwell time of the product mixture in the crystallization is more than 4 hours.

In various embodiments of processes according to the present invention, the processes can be advantageously carried out such that the $1^{st}$ stage of the crystallization comprises at least 50 to 85% of the total crystallization volume of the two-stage crystallization, wherein the total volume of the crystallizers is at least 4 times the product-containing suspension fed into the two-stage crystallization in unit time.

In various embodiments of processes according to the present invention, the processes can be advantageously carried out such that the 1st stage of the crystallization comprises at least 60 to 80% of the total crystallization volume of the two-stage crystallization, wherein the total volume of the crystallizers is at least 4 times the product-containing suspension fed into the two-stage crystallization per hour.

In various embodiments of processes according to the present invention, the processes can be advantageously carried out such that the product-containing suspension fed into the crystallization is composed of 15-40 wt % BPA, 60-85 wt % phenol, 0.5-7 wt % o,p-BPA, 0-5 wt % trisphenols, 0-7 wt % indanes/indenes, 0-7 wt % chromanes/chromenes, 0-5 wt % water, 0-8 wt % acetone, 0-5 wt % o,o-BPA and 0-5 wt % isopropenylphenols, relative to the total weight of the suspension.

In various embodiments of processes according to the present invention, the processes can be advantageously carried out such that the washing is performed at least partially with phenol that originates from the production of polycarbonate by the melting process.

Another embodiment of the present invention includes a process comprising:

(a) reacting phenol and acetone in the presence of an acidic catalyst to form a product mixture comprising 15 to 40 wt % bisphenol A, 60 to 85 wt % phenol, 0.5 to 7 wt % of o,p-bisphenol A, 0 to 5 wt % of one or more trisphenols, 0 to 7 wt % of one or more indanes/indenes, 0 to 7 wt % of one or more chromanes/chromenes, 0 to 5 wt % water, 0 to 8 wt % acetone, 0 to 5 wt % o,o-bisphenol A, and 0 to 5 wt % of one or more isopropenylphenols, the percentages by weight based on the weight of the product mixture;

(b) removing at least a portion of the bisphenol A from the product mixture in the form of a bisphenol A/phenol adduct by crystallization, filtration and washing to provide bisphenol A/phenol adduct crystals; and (c) removing at least a portion of the phenol from the bisphenol A/phenol adduct crystals to provide bisphenol A having a purity of more than 99.7%;

wherein the crystallization comprises continuous suspension crystallization and is carried out in at least three crystallization devices arranged such that the product mixture is first cooled in a first stage of the crystallization to a temperature of 50 to 70° C. in a first crystallization device and a second crystallization device connected in parallel, and subsequently cooled in a second stage of the crystallization to a temperature of 40 to 50° C. in a third crystallization device connected downstream in series to the first and second crystallization devices, wherein a total dwell time of the product mixture in the crystallization is more than 4 hours, wherein a total crystallization volume of the at least three crystallization devices is at least four times the volume of the product mixture fed into the crystallization per hour, and wherein the first stage of the crystallization comprises at least 50 to 85% of the total crystallization volume.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF THE INVENTION

Figure 1:
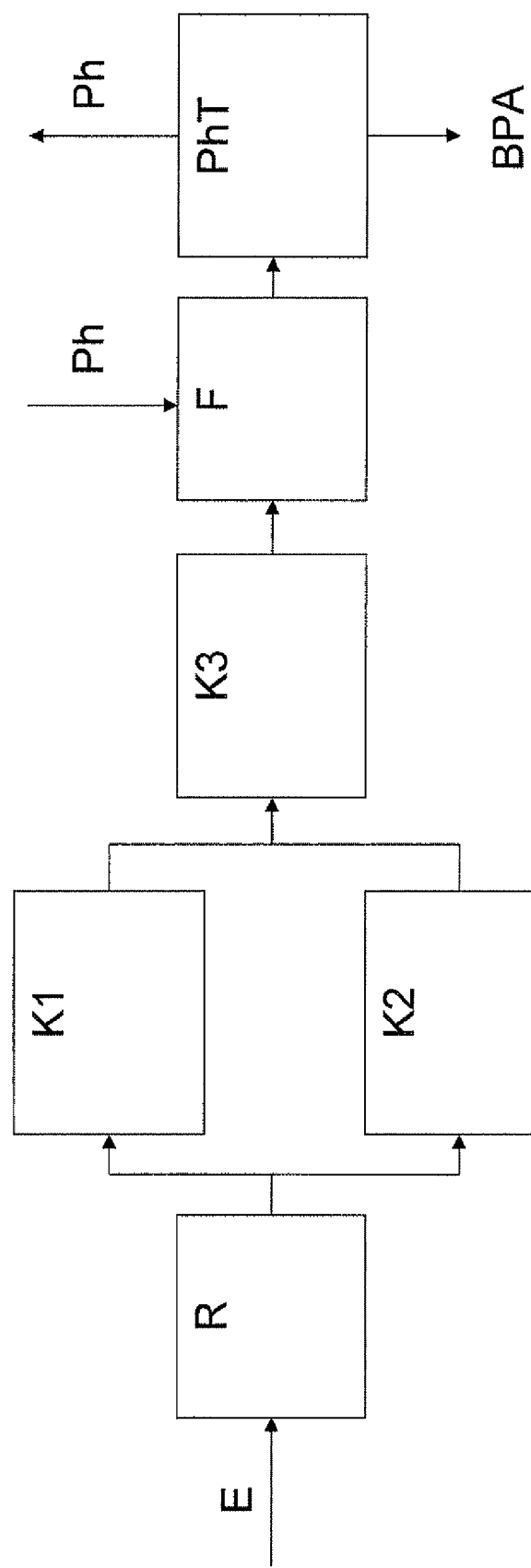
FIG. 1 is diagrammatic flow chart of a process in accordance with one embodiment of the present invention.

As used herein, the singular terms "a" and "the" are synonymous and used interchangeably with "one or more" and "at least one," unless the language and/or context cleary indicates otherwise. Accordingly, for example, reference to "a phenol" herein or in the appended claims can refer to a single phenol or more than one phenol. Additionally, all numerical values, unless otherwise specifically noted, are understood to be modified by the word "about."

In various preferred embodiments of processes according to the present invention, the process can preferably be carried out such that the liquid to be crystallized is cooled, prior to the crystallization, to temperatures below 80° C., preferably to temperatures of 75° C., in particular 75 to >70° C.

The crystallization carried out in the processes according to the invention takes place in at least three crystallization devices that can each comprise a crystallization vessel, a circulating pump and a heat exchanger. Preferably, each crystallization device comprises one or more heat exchangers. Particularly preferably each crystallization device comprises one heat exchanger. The product mixture that has been produced by the reaction of phenol with acetone and out of which the bisphenol A/phenol adduct is crystallized is preferably incorporated in the circulation current immediately prior to the crystallization.

The total volume of all the crystallization devices used is preferably equal to at least 4 times the product-containing suspension volume (i.e., the product mixture) fed into the crystallization per hour.

Crystallization in the various embodiments of processes according to the present invention, can preferably be carried out such that is performed in two stages. In this connection, the first stage comprises at least two crystallization devices connected in parallel. Further crystallization devices can also be connected in addition to these two in the first stage, these additional crystallization devices connected likewise in parallel to the other two. At least 50% of the total crystallization volume over all the stages of the crystallization is preferably carried out in the first stage of the crystallization, more preferably at least 55%, particularly preferably at least 60%. The temperature in the first crystallization stage is generally below 70° C., preferably below 65° C., particularly preferably about 50 to 65° C., very particularly preferably about 50 to 62° C.

In various preferred embodiments of processes according to the present invention, the process can preferably be carried out such that the bisphenol A content of the product mixture inflow to the first crystallization stage is 15 to 40 wt %, more preferably 15 to 35 wt %, particularly preferably 20 to 35 wt %.

In the first crystallization stage, at least two crystallization devices which generally comprise a crystallization vessel, a cooler and a circulating pump are operated in parallel with one another. In various preferred embodiments, the volumetric capacities of the at least two crystallization devices in the first crystallization stage are equal to one another. Preferably, the volumetric capacity of the crystallization devices of the first stage is at least 20% greater than that of the second stage and, particularly preferably, the volumetric capacity in the first stage is at least one and a half times as great as that of the second stage. In various particularly preferred embodiments, the volumetric capacities of all the crystallization devices are equal to one another. Thus, in various embodiments wherein the first stage comprises two crystallization devices and the second stage comprises one crystallization device, each of the three devices having an equal volumetric capacity, the total volumetric capacity of the first stage is two times that of the second stage.

In the second crystallization stage, at least one crystallization device is connected in series with the first two crystallization devices. The temperature in the crystallization device of the second stage is lower than in the first stage, preferably below 50° C., particularly preferably below 45° C., very particularly preferably about 40 to 43° C. Preferably, upon leaving the second crystallization stage, which comprises at least one crystallization device connected in series with the crystallization devices of the first stage, the content of bisphenol A in dissolved form in the mother liquor leaving the last crystallization device of the second stage is 5 to 20 wt %, relative to the total weight of the liquid mother liquor, more preferably 5 to 15 wt %.

The suspension obtained from the second crystallization stage is then filtered, a bisphenol A/phenol adduct being obtained that is purified by washing operations known to the person skilled in the art and then separated into bisphenol A and phenol by separative operations known to the person skilled in the art, such as, for example, evaporation, distillation or stripping. A bisphenol A having a purity greater than 99.7%, relative to the total amount of product obtained with the exclusion of phenol still contained, can be obtained in this way by the processes according to the invention.

The processes according to the invention for producing crystals of adducts composed of bisphenol A and phenol can provide the adducts of bisphenol A and phenol in such a high purity that the further working-up steps normally necessary for producing a bisphenol A suitable for high-quality secondary products, for example polycarbonates, epoxy resins, formaldehyde resins etc. can be avoided. The said further working-up steps normally necessary are, for example, additional crystallization steps or additional distillation steps.

A further advantage of the processes according to the invention is that the longer dwell times available in the high-temperature stage reduce the supersaturation in said crystallization stage, as a result of which the heat exchangers have to be cleaned less often of adhering deposits that have crystallized out.

A further advantage of the processes according to the invention is that, as a result of the parallel mode of operation of the crystallizers in the first stage, a further crystallizer remains in operation at the same temperature stage during the melting down of a crystallizer, thereby avoiding a changeover to single-stage crystallization having an exclusive low temperature stage. This can increase the system availability and also, at the same time, the product purity.

A further advantage of the processes according to the invention is the maintenance of a higher production capacity if, as a result of the production operation, heat exchangers are already partially coated with adhering deposits that have crystallized out. Since the deposits that have partially crystallized out in the heat exchanger adversely affect the heat transmission, this has to be compensated for during constant production output by reducing the cooling water temperature. This results in turn in an accelerated coating of the heat exchanger with deposits crystallizing out and consequently in a more frequently needed melting-down of the crystallizer. In the case of a partially coated heat exchanger, the production volumetric flow can be matched to the respective degree of coating of the heat exchanger as a result of the process according to the invention and, in this way, the production output can be kept a high level with simultaneous maintenance of the product quality.

In various preferred embodiments of processes according to the present invention, the crystallization of the adduct composed of a bisphenol and a phenol can be carried out such that the heat exchangers (e.g., circulating coolers) are operated with temperature-controlled hot water as a cooling medium. In this regard, it is preferable, in particular, that the temperature difference between the temperature-controlled hot water and the product mixture to be cooled is <8 K, very particularly preferably <5 K.

In various preferred embodiments of processes according to the present invention, the crystallization of the adduct composed of a bisphenol and a phenol can be carried out such that a crystallizer in the first stage and the associated peripheral appliances are cleaned at regular time intervals of preferably 25 to 60 days by heating preferably to 80° C. or higher, while operation of the circulating system is continued using the other parallel-arranged crystallization device of the first stage.

In various preferred embodiments of processes according to the present invention, the crystallization of the adduct composed of a bisphenol and a phenol can be carried out as a suspension crystallization, preferably in the form of a circulation crystallization.

Bisphenols other than bisphenol A can also be produced by the process according to the invention. Accordingly, it is to be understood that exemplary references herein to processes for producing bisphenol A apply equally to processes for the production of other bisphenols.

Unsubstituted phenol is preferably used for the processes according to the invention. Other bisphenols can be produced by the processes according to the invention by use of corresponding phenol derivatives.

In various preferred embodiments of processes according to the present invention, a product mixture (i.e., suspension)

comprising the following constituents, percentages by weight being based on the total weight of the suspension, is fed to the crystallization:

BPA: 15-40 wt %, preferably 15-35 wt %, more preferably 20-35 wt %;

phenol: 60-85 wt %, preferably 65-85 wt %, more preferably 65-80 wt %;

o,p-BPA: 0.5-7 wt %, preferably 1-6 wt %, more preferably 1-5 wt %;

trisphenols: 0-5 wt %, preferably 0-3 wt %;

indanes/indenes: 0-7 wt %, preferably 0-5 wt %;

chromanes/chromenes: 0-7 wt %, preferably 0-5 wt %;

water: 0-5 wt %, preferably 0-3 wt %;

acetone: 0-8 wt %, preferably 0-5 wt %, more preferably 0-2 wt %, o,o-BPA: 0-5 wt %, preferably 0-3 wt %;

isopropenylphenols: 0-5 wt %, preferably 0-3 wt %.

Optionally, the product mixture can be freed completely or partially of water contained in it, unreacted acetone and other lower-boiling compounds before the suspension crystallization by distillation, preferably vacuum distillation.

The mixed bisphenol A/phenol crystals (bisphenol A/phenol adduct) can be separated from the mother liquor by the use of filter media suitable for removing solids. Preferably, a washing of the solid removed is also possible in or on these apparatuses. This can be achieved, for example, in suitable centrifuges, such as skimmer centrifuges, screen-conveyor centrifuges or push-type centrifuges, but also on rotary filters, belt filters and (vacuum) disc filters. Preferably, pressurized rotary filters, particularly preferably rotary vacuum filters are used.

The washing of the solid removed (filter cake) can also be performed separately in a suitable apparatus following the solid/liquid separation.

The filter cake of the mixed bisphenol A/phenol crystals can be washed with fresh phenol and/or phenol fed back from the bisphenol A production process that has optionally been distillatively purified beforehand. The washing is preferably performed at a phenol temperature of 40-70° C.

Phenol that accumulates in the production of polycarbonate by the melting process can also be used for washing.

The washed mixed crystals can then preferably be melted and the melt obtained freed of the phenol as known from the prior art. Preferably, the melt is freed of phenol and other readily volatile impurities in a two-stage operation. In this case, the melt is treated in a first step with both a vacuum and an elevated temperature and in a second step with a desorption gas, preferably nitrogen, at a temperature of 160-210° C., in which process phenol is removed down to residual contents of <200 ppm.

In another preferred embodiment, the phenol can be removed only in one stage at elevated temperature and in vacuo, in which process residual contents of phenol in the bisphenol of up to 10 wt % relative to the total amount of product can be established.

Bisphenol A produced by the processes according to the invention can be reacted with phosgene by the interface process or with diaryl carbonates, preferably diphenyl carbonate, by the melting process to form polycarbonate. The BPA produced by the processes according to the invention can furthermore serve as starting material for producing various polymeric materials, such as, for example, polyarylates, polyetherimides, modified phenolformaldehyde resins and epoxy resins.

The invention will now be described in further detail with reference to the following non-limiting examples.

EXAMPLES

FIG. 1 diagrammatically describes an embodiment according to the invention, in which three crystallization devices (K1, K2 and K3) are used, of which the first two (K1 and K2) are operated in parallel and the third (K3) is connected in series with said first two.

Figure 2:
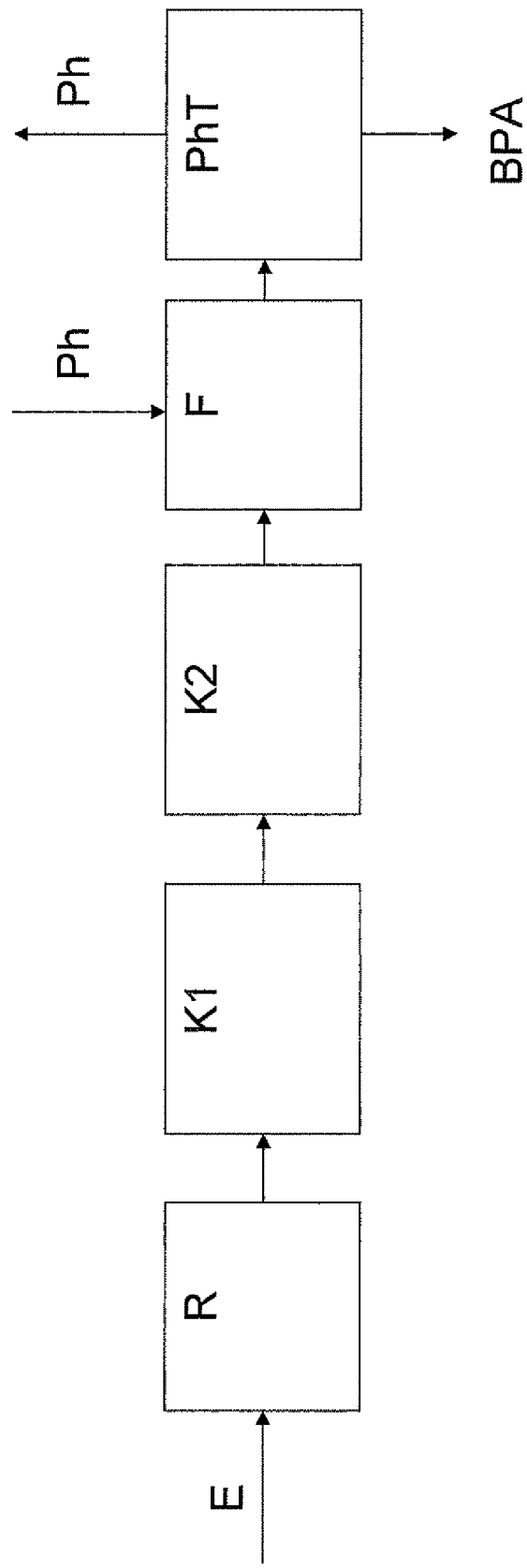
FIG. 2 is diagrammatic flow chart of a comparative process.

FIG. 2 diagrammatically describes a method in which only two crystallization devices (K1 and K2), which are connected in series, are used.

In the figures:
R denotes a reaction vessel or reactor arrangement in which the bisphenol A production is performed,
E denotes the feed for the bisphenol A production,
K1 denotes crystallization device 1 (also denoted as cystallizer 1 for short),
K2 denotes crystallization device 2 (also denoted as cystallizer 2 for short),
K3 denotes crystallization device 3 (also denoted as cystallizer 3 for short),
F denotes filtration,
PhT denotes phenol separation,
Ph denotes phenol,
BPA denotes bisphenol A.

Example 1

In Accordance with the Invention

In FIG. 1, the reaction mixture from the BPA production R was fed to a suspension crystallization in a device arrangement comprising three crystallization devices (K1, K2 and K3 in accordance with FIG. 1) for the purpose of working up and purifying BPA. For this purpose, a 2-stage crystallization was performed, starting in the 1st stage at 54° C. and continued in the 2nd stage at 41° C., the 1st stage comprising two crystallization devices (K1 and K2) operated in parallel and the 2nd stage comprising one crystallization device (K3) whose volume was 80% of the sum of the crystallization devices K1 and K2 of the 1st stage. The bisphenol A content of the reaction solution to be crystallized was 30%. The reaction mixture was added at 70° C. to the circulation current immediately upstream of the crystallization devices K1 and K2.

The circulating coolers were fed from top to bottom and the coolers were operated with temperature-controlled hot water. The maximum temperature difference between the temperature-controlled hot water and the suspension to be cooled was 3 K.

The prepared mixed-crystal suspension was removed from the crystallizer K3 after a total dwell time in all the crystallizers of 8.5 hours.

For the procedure, tube-bank heat exchangers were used as heat exchangers. No impairment of the heat transmission due to deposits on the inner surfaces of the cooling tubes was observed within a time interval of 3 months, with the result that the inner surfaces of the cooling tubes did not have to be freed from BPA coatings and BPA/phenol coatings during said time interval.

It was possible to obtain bisphenol A/phenol adduct crystals having high purities by this type of crystallization.

After filtration F and phenol separation PhT, bisphenol A (BPA) having a purity of 99.75% and a Hazen colour index of about 15 was obtained. The Hazen colour index was determined visually by comparison with APHA standard colorimetry solutions in accordance with ASTM D 1209-97.

Example 2

According to the Invention

In FIG. 1, the reaction mixture from the BPA production R was fed to a suspension crystallization in a device arrangement comprising three crystallization devices (K1, K2 and K3 in accordance with FIG. 1) for the purpose of working up and purifying BPA. For this purpose, a 2-stage crystallization was performed, starting in the 1st stage at 54° C. and continued in the 2nd stage at 41° C., the 1st stage comprising two crystallization devices (K1 and K2) operated in parallel and the 2nd stage comprising one crystallization device (K3) whose volume was 50% of the sum of the crystallization devices K1 and K2 of the 1st stage. The bisphenol A content of the reaction solution to be crystallized was 30%. The reaction mixture was added at 70° C. to the circulation current immediately upstream of the crystallization devices K1 and K2.

The circulation current of the circulating crystallization was fed tangentially to the foot of the respective crystallization vessel and removed centrally at the head of the respective crystallization vessel.

The circulating coolers were fed from top to bottom and the coolers were operated with temperature-controlled hot water. The maximum temperature difference between the temperature-controlled hot water and the suspension to be cooled was 3 K, The prepared mixed-crystal suspension was removed from the crystallizer K3 after a total dwell time in all the crystallizers of 8.5 hours.

For the procedure, tube-bank heat exchangers were used as heat exchangers. No impairment of the heat transmission due to deposits on the inner surfaces of the cooling tubes of the heat exchanger was observed within a time interval of 10 months, with the result that the inner surfaces of the cooling tubes did not have to be freed from BPA coatings and BPA/phenol coatings during said time interval.

After filtration F and phenol separation PhT, bisphenol A (BPA) having a purity of 99.79% and a Hazen colour index of <15 was obtained. The Hazen colour index was determined visually by comparison with APHA standard colorimetry solutions in accordance with ASTM D 1209-97.

It was possible to obtain bisphenol A/phenol adduct crystals having high purities by this type of crystallization according to the invention. As a result of the choice of the volume of the crystallization device in the second stage, it was possible to increase the purity even further compared with Example 1.

Example 3

Comparison Example

In FIG. 2, the reaction mixture from the BPA production R was fed to a suspension crystallization in a device arrangement comprising two crystallization devices (K1 and K2 in accordance with FIG. 2) for the purpose of working up and purifying BPA. For this purpose, a 2-stage crystallization was performed, starting in the 1st stage at 54° C. and continued in the 2nd stage (K2) at 41° C., both stages in the crystallization devices (K1 and K2) having the same crystallization volumes. The bisphenol A content of the reaction solution to be crystallized was 30%. The reaction mixture was added at 70° C. to the circulation current immediately upstream of the crystallization device K1.

The circulation current of the circulating crystallization was fed tangentially to the foot of the respective crystallization vessel and removed centrally at the head of the respective crystallization vessel.

The circulating coolers were fed from top to bottom and the coolers were operated with temperature-controlled hot water. The maximum temperature difference between the temperature-controlled hot water and the suspension to be cooled was 3 K.

The prepared mixed-crystal suspension was removed from K2 after a total dwell time in all the crystallizers of 8.5 hours.

For the procedure, tube-bank heat exchangers were used as heat exchangers. To free them from BPA coatings and BPA/phenol coatings, the inner surfaces of the cooling tubes had to be cleaned at approximately 2-monthly intervals by a rapid heating to 80° C. or, alternatively, the entire crystallization device system had to be cleaned by heating the product content and continued operation of the circulation system.

After filtration F and phenol separation PhT from the bisphenol A/phenol adduct crystals obtained in this way, bisphenol A (BPA) having a purity of 99.72% and a Hazen colour index of 20 was obtained. The Hazen colour index was determined visually by comparison with APHA standard colorimetry solutions in accordance with ASTM D 1209-97.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising:
   (a) reacting a phenol and acetone in the presence of an acidic catalyst to form a product mixture comprising a bisphenol;
   (b) removing at least a portion of the bisphenol from the product mixture in the form of a bisphenol/phenol adduct by crystallization, filtration and washing to provide bisphenol/phenol adduct crystals; and
   (c) removing at least a portion of the phenol from the bisphenol/phenol adduct crystals to provide the bisphenol having a purity of more than 99.7%;
   wherein the crystallization comprises continuous suspension crystallization and is carried out in at least three crystallization devices arranged such that the product mixture is first cooled in a first stage of the crystallization to a temperature of 50 to 70° C. in a first crystallization device and a second crystallization device connected in parallel, and subsequently cooled in a second stage of the crystallization to a temperature of 40 to 50° C. in a third crystallization device connected downstream in series to the first and second crystallization devices, and wherein a total dwell time of the product mixture in the crystallization is more than 4 hours.

2. The process according to claim 1, wherein the bisphenol comprises bisphenol A.

3. The process according to claim 1, wherein the product mixture is cooled to a temperature below 80° C. prior to the first stage of the crystallization.

4. The process according to claim 1, wherein each of the at least three crystallization devices comprises a heat exchanger having a cooling medium, and wherein a temperature difference between the cooling medium and the product mixture being cooled is less than 8° K.

5. The process according to claim 1, wherein a total crystallization volume of the at least three crystallization devices is at least four times the volume of the product mixture fed into the crystallization per hour, and wherein the first stage of the crystallization comprises at least 50 to 85% of the total crystallization volume.

6. The process according to claim 5, wherein the product mixture is cooled to a temperature below 80° C. prior to the first stage of the crystallization.

7. The process according to claim 2, wherein a total crystallization volume of the at least three crystallization devices is at least four times the volume of the product mixture fed into the crystallization per hour, and wherein the first stage of the crystallization comprises at least 50 to 85% of the total crystallization volume.

8. The process according to claim 7, wherein the product mixture is cooled to a temperature below 80° C. prior to the first stage of the crystallization.

9. The process according to claim 8, wherein each of the at least three crystallization devices comprises a heat exchanger having a cooling medium, and wherein a temperature difference between the cooling medium and the product mixture being cooled is less than 8° K.

10. The process according to claim 1, wherein a total crystallization volume of the at least three crystallization devices is at least four times the volume of the product mixture fed into the crystallization per hour, and wherein the first stage of the crystallization comprises at least 60 to 80% of the total crystallization volume.

11. The process according to claim 1, wherein the product mixture fed into the crystallization comprises 15 to 40 wt % bisphenol A, 60 to 85 wt % phenol, 0.5 to 7 wt % of o,p-bisphenol A, 0 to 5 wt % of one or more trisphenols, 0 to 7 wt % of one or more indanes/indenes, 0 to 7 wt % of one or more chromanes/chromenes, 0 to 5 wt % water, 0 to 8 wt % acetone, 0 to 5 wt % o,o-bisphenol A, and 0 to 5 wt % of one or more isopropenylphenols, the percentages by weight based on the weight of the product mixture.

12. The process according to claim 11, wherein a total crystallization volume of the at least three crystallization devices is at least four times the volume of the product mixture fed into the crystallization per hour, and wherein the first stage of the crystallization comprises at least 50 to 85% of the total crystallization volume.

13. The process according to claim 12, wherein the product mixture is cooled to a temperature below 80° C. prior to the first stage of the crystallization.

14. The process according to claim 13, wherein each of the at least three crystallization devices comprises a heat exchanger having a cooling medium, and wherein a temperature difference between the cooling medium and the product mixture being cooled is less than 8° K.

15. The process according to claim 1, wherein the washing is carried out with phenol, and wherein at least a portion of the phenol is obtained from a melt production of polycarbonate.

16. A process comprising:
(a) reacting phenol and acetone in the presence of an acidic catalyst to form a product mixture comprising 15 to 40 wt % bisphenol A, 60 to 85 wt % phenol, 0.5 to 7 wt % of o,p-bisphenol A, 0 to 5 wt % of one or more trisphenols, 0 to 7 wt % of one or more indanes/indenes, 0 to 7 wt % of one or more chromanes/chromenes, 0 to 5 wt % water, 0 to 8 wt % acetone, 0 to 5 wt % o,o-bisphenol A, and 0 to 5 wt % of one or more isopropenylphenols, the percentages by weight based on the weight of the product mixture;
(b) removing at least a portion of the bisphenol A from the product mixture in the form of a bisphenol A/phenol adduct by crystallization, filtration and washing to provide bisphenol A/phenol adduct crystals; and
(c) removing at least a portion of the phenol from the bisphenol A/phenol adduct crystals to provide bisphenol A having a purity of more than 99.7%;
wherein the crystallization comprises continuous suspension crystallization and is carried out in at least three crystallization devices arranged such that the product mixture is first cooled in a first stage of the crystallization to a temperature of 50 to 70° C. in a first crystallization device and a second crystallization device connected in parallel, and subsequently cooled in a second stage of the crystallization to a temperature of 40 to 50° C. in a third crystallization device connected downstream in series to the first and second crystallization devices, wherein a total dwell time of the product mixture in the crystallization is more than 4 hours, wherein a total crystallization volume of the at least three crystallization devices is at least four times the volume of the product mixture fed into the crystallization per hour, and wherein the first stage of the crystallization comprises at least 50 to 85% of the total crystallization volume.

17. The process according to claim 16, wherein the product mixture is cooled to a temperature below 80° C. prior to the first stage of the crystallization.

18. The process according to claim 17, wherein each of the at least three crystallization devices comprises a heat exchanger having a cooling medium, and wherein a temperature difference between the cooling medium and the product mixture being cooled is less than 8° K.

* * * * *